United States Patent [19]

Barge

[11] Patent Number: 4,534,076
[45] Date of Patent: Aug. 13, 1985

[54] RECLINING RADIOGRAPHIC WALL TABLE

[76] Inventor: Fred H. Barge, 322 Cameron Ave., LaCrosse, Wis. 54601

[21] Appl. No.: 375,531

[22] Filed: May 5, 1982

[51] Int. Cl.³ .............................................. A47C 19/06
[52] U.S. Cl. ......................................... 5/147; 5/136; 5/133; 378/209
[58] Field of Search ..................... 5/62, 133, 137, 139, 5/145–148, 60, 80, 444; 378/209

[56]  References Cited
U.S. PATENT DOCUMENTS

| | | | |
|---|---|---|---|
| 698,626 | 4/1902 | Brekke | 5/444 |
| 1,506,525 | 8/1924 | Hegedus | 5/62 |
| 2,536,212 | 1/1951 | Ostroff | 378/209 |
| 2,887,691 | 5/1959 | Talarico et al. | 5/145 |
| 3,441,014 | 4/1969 | Ramsey | 5/62 |
| 3,703,735 | 11/1972 | Moore | 5/147 |
| 3,783,863 | 1/1974 | Kliever | 378/209 |
| 4,214,327 | 7/1980 | Smith | 5/444 |
| 4,310,935 | 1/1982 | Stevens et al. | 5/80 |

Primary Examiner—Gary L. Smith
Assistant Examiner—Michael F. Trettel
Attorney, Agent, or Firm—Harvey B. Jacobson

[57] ABSTRACT

Reclining radiographic wall table assembly including a wall mounted rack, a wheeled bed table having floor engaging wheels mounted at one end of the table and a rack engaging member at the other for engaging the wall mounted rack, and a control mechanism providing control of the positioning of the table so that it is selectively oriented either horizontally, vertically, or in a semi-reclining position intermediate the first two positions. The table is also provided with an ankle holding attachment mounted on the surface of the table near the rack engaging member for securing a patient onto the table when the table is in an inclined or vertical position, the patient then being inverted while being X-rayed for determining an amount of the scoliotic bend capable of being attributed to the gravitational pull upon the patient were the patient standing in an essentially upright position. Greater versatility and use of X-ray equipment is achieved by use of the assembly and the holding attachment for the patient heretofore not available.

5 Claims, 7 Drawing Figures

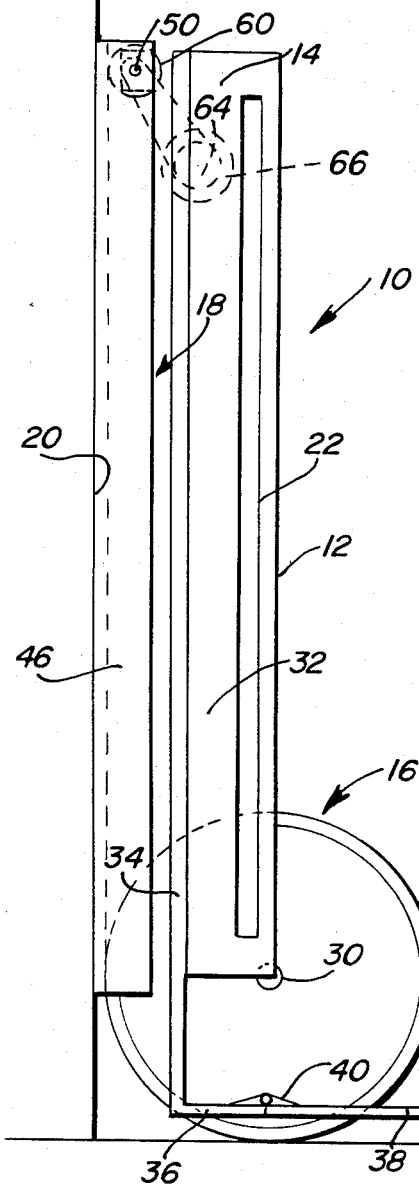
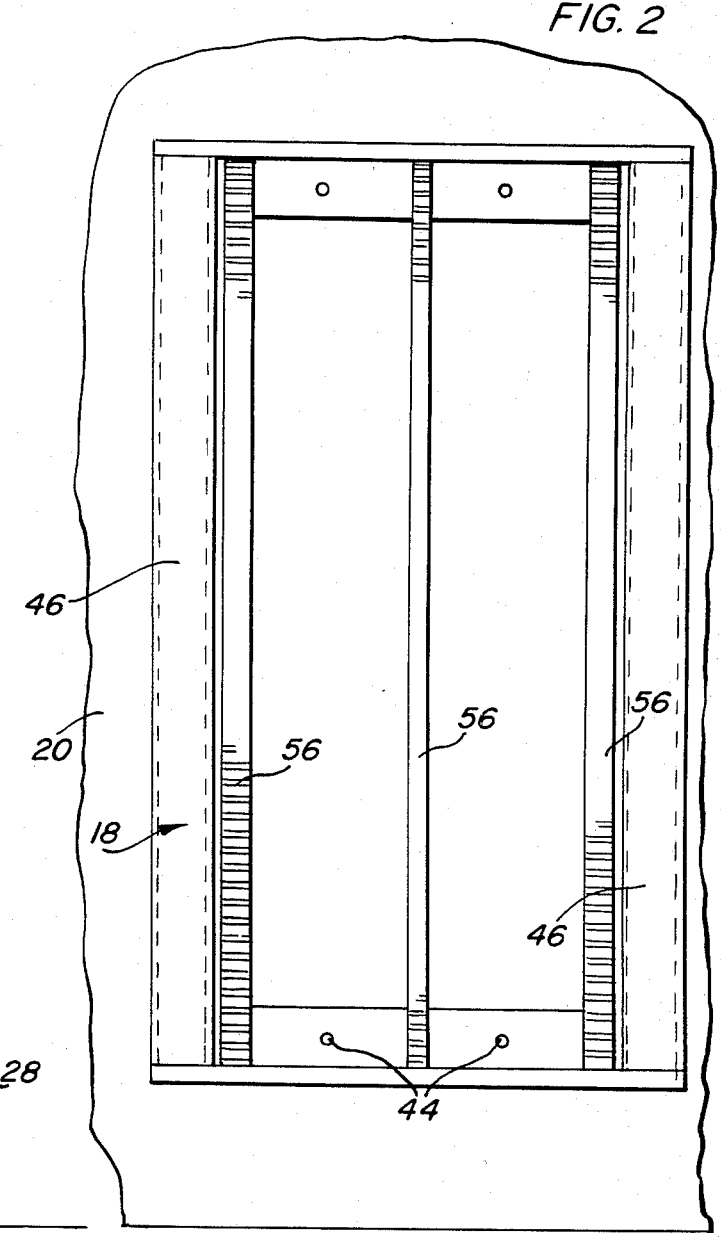
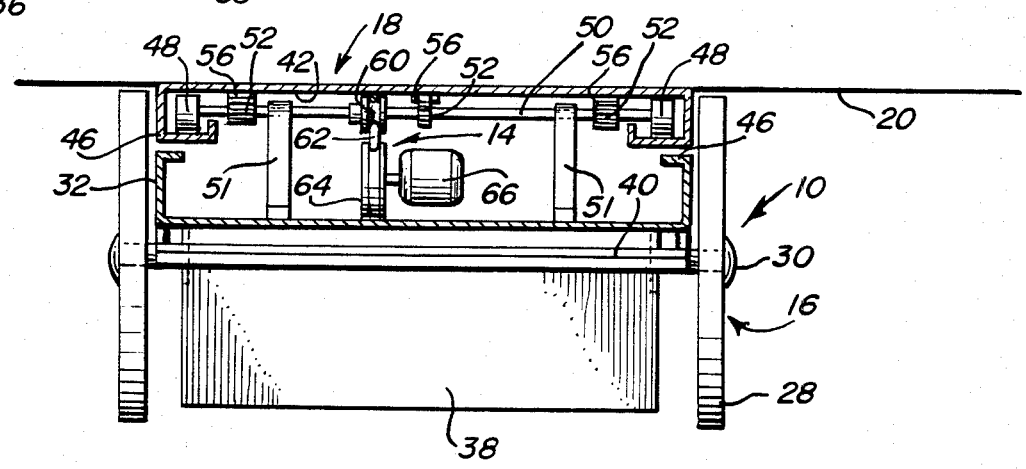
FIG. 1
FIG. 2
FIG. 3

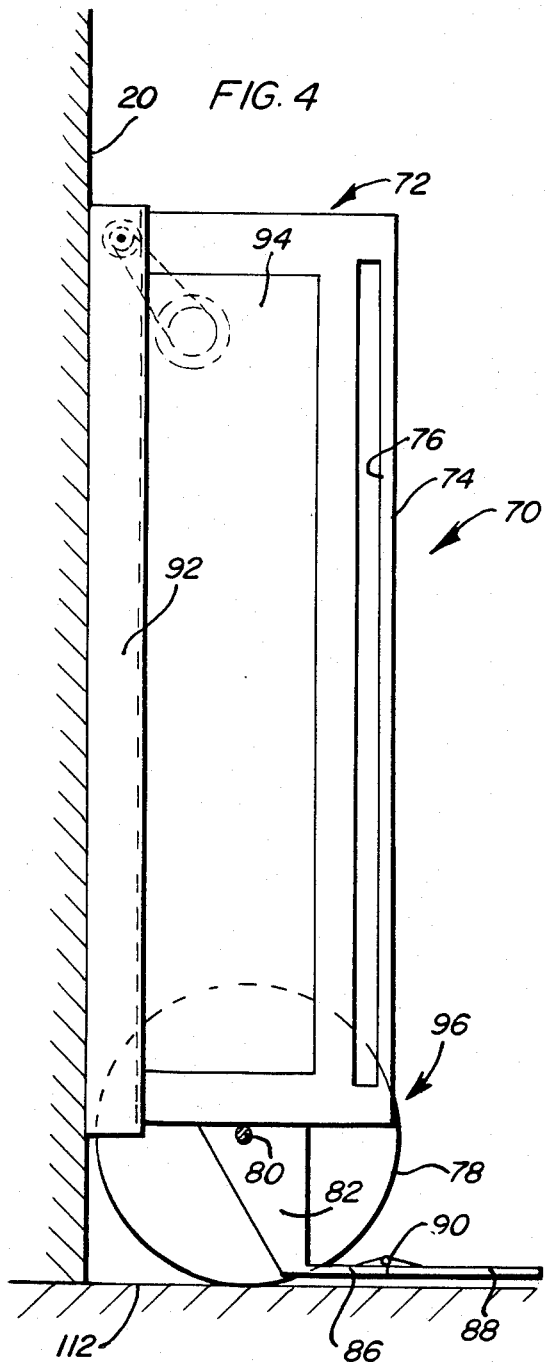
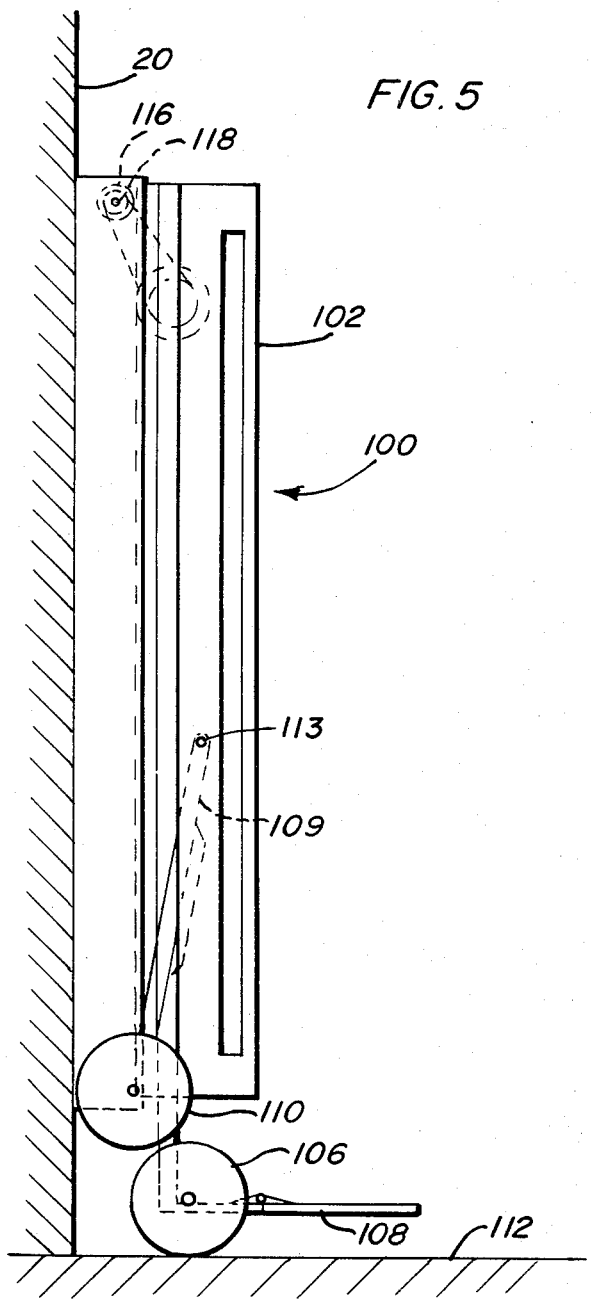

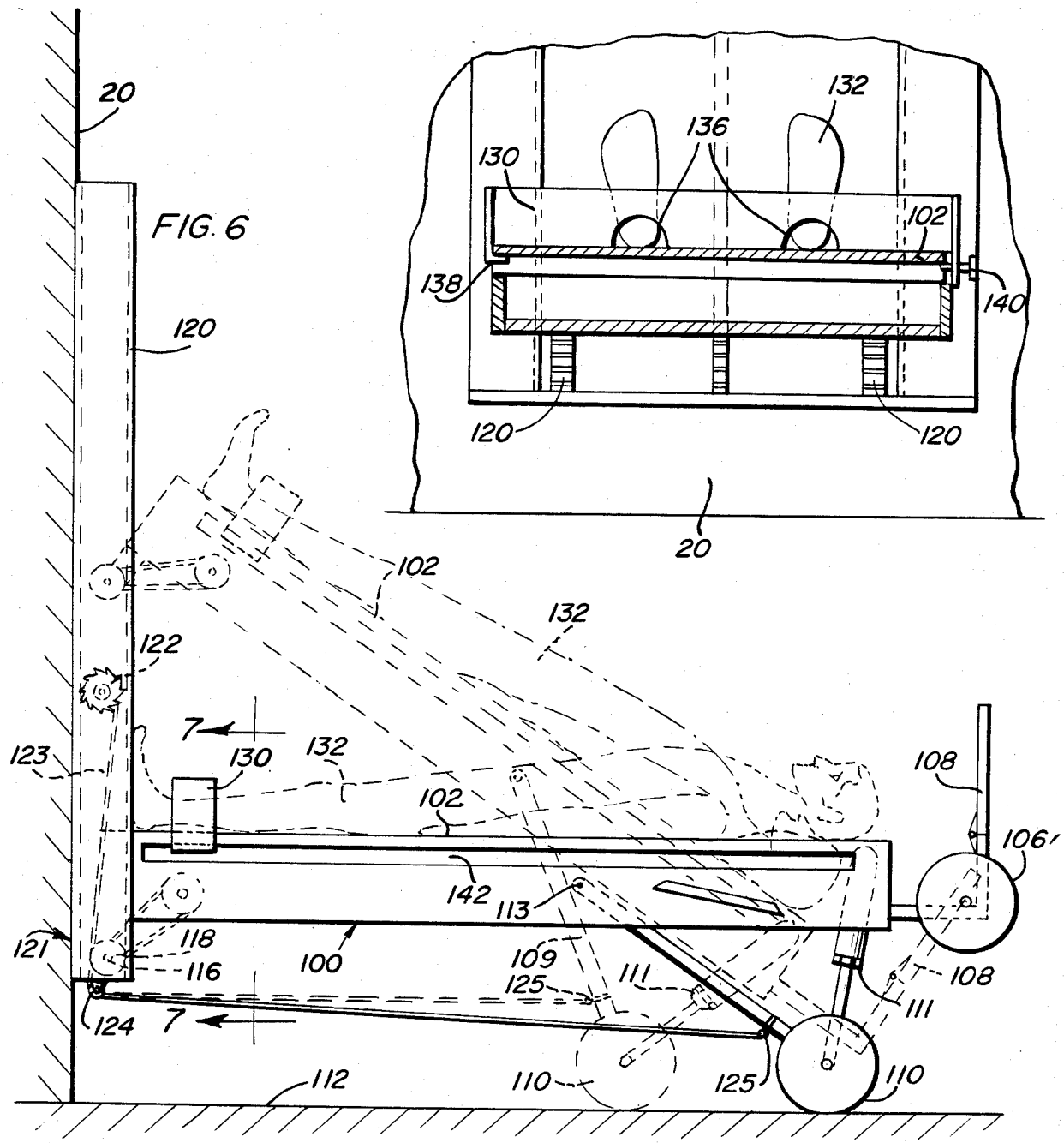

RECLINING RADIOGRAPHIC WALL TABLE

BACKGROUND OF THE INVENTION

The present invention relates to a radiographic table capable of being adjusted from a full upright position to a full horizontal position and capable of being interpositioned at selected intervals between the first two positions. In addition, the invention is provided with a patient holding member for holding the patient on the surface of the table in an inverted position so that the patient is capable of being X-rayed for determining how much of a scoliotic bend or deformation of the patient's spine may be attributed to the force due to gravity or what is called or defined herein as the gravitational pull. It has been theorized that upon hanging by one's arms and then being X-rayed, the curve shown on the X-ray could be attributed to structural changes, and where the table could be fully reclined and the patient placed upon it, an ankle bar or member fixed for holding the patient in place by the heels against the table, subsequently raising the table up any significant degree of inversion, it is found desirable that the X-ray product would indicate and determine how much of the scoliotic bend or deformation, if any, is attributable to gravitational pull, or how much of the scoliotic bend is attributable to other causes.

1. Field of the Invention

In X-raying of scoliotic spines, it is important that a patient be X-rayed in an upright posture with weight upon the feet and for thereby determining the amount of gravitational effect, if any, is due upon the scoliotic spine. Such effects can also determine an effect of unilateral short leg upon the scoliotic spine. Placement of the patient standing before a conventional wall mounted unit is difficult to duplicate when X-rays are retaken of the patient and yet displacement can influence the image of the scoliotic angles. In a semi-reclining position, for instance a 10° incline with respect to the vertical, weight upon the feet would be maintained and consistent placement of the patient against the radiographic table would be maintained by gravitational pull. In this way, retaking X-rays to determine the progress or the change in the scoliotic curves will be more accurate.

The table assembly of the invention may be moved and stopped at any position between full vertical and full horizontal, facilitating the bucky tube or cassette alignment of specific views of the patient that need to be taken by X-ray. As an example, taking of an X-ray of the superior body surface of the sacrum or sacral base X-ray, would be quite easy to accomplish with the table assembly of the present invention. The table could be reclined to any angle necessary to take the view while maintaining weight bearing upon the feet of the patient.

In scoliotic patients, the degree of functional versus structural involvement of the scoliotic curves has been evaluated by having a patient hang by a bar and then be subject to X-rays. With the attachment of the present invention, the patient could be inverted on the table and X-rayed while in an inverted position for determining how much of the scoliotic bend or spine could be attributed to the gravitational pull. The table assembly of the present invention contains a radiographic bucky capable of handling cassettes of X-ray film such as those denominated as 14×36 and 14×17. The bucky slides up and down within the table to accommodate different patient heights for sizes of the patients or for other convenient adjustments.

2. Description of the Prior Art

Various prior U.S. patents of interest are as follows: U.S. Pat. Nos.
- 371,871—Oct. 18, 1887—Ayres
- 456,915—July 28, 1891—Stevens
- 1,925,425—Sept. 5, 1933—Wilent
- 2,024,351—Dec. 17, 1935—Fischer et al
- 3,517,397—June 30, 1970—Moore
- 3,532,882—Oct. 6, 1970—Craig et al
- 3,703,735—Nov. 28, 1972—Moore
- 3,711,878—Jan. 23, 1973—George et al
- 3,806,109—Apr. 23, 1974—Weber et al
- 3,851,644—Dec. 3, 1974—Slagle
- 4,013,019—Mar. 22, 1977—Horsey
- 4,131,801—Dec. 26, 1978—Hogan.

The patents to Wilent, Fischer et al, Craig et al, Weber et al, Slagle, Horsey and Hogan disclose pivotal mounted X-ray operating tables for taking X-rays when the table is in a vertical, horizontal and inclined position. The patent to George et al discloses a bed stored in a tilted, non-usable position, the bed being secured by projections to an endless chain driven by a coin operated clock driving a motor. The patents to Moore disclose retracting bed mechanisms and the patents to Ayres and Stevens disclose wall or closeted folding beds. None of the patents disclose features that bear upon the patentability of the claims of the present invention.

SUMMARY OF THE INVENTION

An advantage and object of the present invention is to provide an improved radiographic table and in which there is provided an adjustably oriented reclining radiographic wall table, the table being capable of being stably oriented from a vertical to a horizontal position as well as in selected intermediate positions between the horizontal and the vertical position.

Another object and advantage of the present invention is to provide an adjustable reclining radiographic wall table that will accept 17×17 and 14×36 buckies or X-ray film cartridges, particularly the table assembly of the present invention is for use in medical offices where an efficient use of space is a prime consideration. Essentially, such objects of the invention are to provide a vertical wall frame for a radiographic table and in which it reclines to create a stable straight radiographic table while in its horizontal position.

A further and additional object of the present invention is to provide medical, chiropractic and osteopathic tables consisting of a vertical wall frame and table for use in X-ray and radiographic purposes while the patient is standing, adjusting the table to a horizontal position for prone or supine X-ray uses.

Yet still an additional object of the present invention is to provide an arrangement in which a table is usable while in the horizontal position and cooperates with a wall frame while in the vertical position but yet is capable of reclining to the horizontal radiographic table by the mechanism so converting it within the scope of the present invention. These advantages provide for less expensive costs than where a horizontal and vertical table are each fixedly installed for radiographic uses in medical and similar offices and also provides for conservation of space which is often a prime consideration, and an object also provides for the table being stopped in a semi-reclining position for providing better table and X-ray angles for specific radiographic views, especially of the spine, where it is desirable to tilt the table when used with a holding mechanism for obtaining an inverted X-ray picture for determining how much of the scoliotic bend is capable of being attributed to gravitational pull and structural change. Particularly, the table of the present invention has application to medical, chiropractic and osteopathic offices and the like, and is particularly useful in areas of chiropractic practice for scoliotic X-rays, X-rays sized 14×36, sacral base or specific cervical X-rays.

It is a final object and advantage of the present invention to provide an adjustably disposed patient support surface for use in X-ray practice, whether the surface is a horizontal table or it is an inclined wall frame and table, and in which the X-ray film cartridges or buckies are as movable therein within the presently available degree of movability of the bucky within the table.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a side elevational view of one embodiment of the present invention illustrating the table in vertical position.

FIG. 2 is a front elevational view of the rack mounted on the wall shown in FIG. 1.

FIG. 3 is a transverse sectional view of an enlarged scale of the arrangement shown in FIG. 1.

FIGS. 4 and 5 are side elevational views of other arrangements than that shown in FIG. 1.

FIG. 6 is a side elevational view of the embodiment of FIG. 5 illustrating alternative positions of the table according to the present invention.

FIG. 7 is a sectional view taken along line 7—7 of FIG. 6.

DESCRIPTION OF THE PREFERRED EMBODIMENT

Referring now to FIGS. 1–3 of the drawings, there is shown a reclining radiographic table arrangement 10 having a table 12, and rolling engaging members 14, 16 for angularly displacing the table relative to a rack 18 mounted on a wall 20.

The table 12 combines the utility of a full upright 14×36/14×17/17×17 x-ray bucky or radiographic cassette 22 provided for controllably sliding up and down within the table 12 to accommodate heights of different patients. The bucky or cassettes are movable within the table 12 in a conventional manner so that the cassettes have a certain degree of movability within the table, whether the table is in a vertical or horizontal orientation.

In FIGS. 1–3, the table 12 is adapted to be positioned in a reclining position from the vertical position shown. The table 12 has a pair of 28 inch wheels 28 journaled thereon so that when the table is horizontally oriented, the table achieves a 14 inch height and the construction of the wheels 28 extend the lower end of the table 12 a distance of 14 inches out from the wall at the base thereof. The wheels 28 pivot about a shaft 30 mounted on a table frame 32 which in turn is affixed to a support plate 34 extending from one end of the table 12 to an angle member 36 extending below the bottom of the table 12 when oriented vertically. The end of the angle member 36 has a patient stand platform 38 connected thereto by a hinge member 40 that restricts the platform 38 from pivoting beyond a horizontal position.

The rack 18 has a wall plate or frame 42 with a plurality of bolt or screw receiving holes 44 shown in FIG. 2 for receiving screws to mount the wall plate 42 on the wall 20. The rack has a set of oppositely disposed recesses or channels 46 receiving rollers or wheels 48 rotatably mounted upon a shaft 50 that is rotatably supported from table frame 32 by brackets 51. A set of gears 52 are fixed to shaft 50 and each gear meshes with a rack gear 56 mounted on plate 42. Also mounted on the shaft 50 is a pulley 60 driven by belt 62 coupled to pulley 64 driven by a motor 66 which may be any electric motor, hydraulic motor, or compressed air motor, as well known in the art. By means of controlling the motor 66, the shaft 50 engaging the rack gear 56 through gears 52, provide for displacement of the gears 52 along the rack gear 56 so that the shaft 50 shown at the top in FIG. 1 may move the entire length of the rack gear so that the table is displaced from the vertical position shown and moved into a horizontal orientation (not shown) with the wheels 28 supporting the end of table remote from gears 52. The patient standing upon the platform 38 and resting or leaning against the table 12 may be oriented in any position from the vertical position to horizontal position described above by actuation of the motor 66 so the gears 52 on the shaft 50 move throughout the entire length of the rack gears 56. In this way, the motor unit, gears and wheels 52, 48 drive and guide the table up and down, respectively, from the vertical to the horizontal orientation. The end wheels 48 roll within the track formed by the recess 46 so that the gears 52 engage the rack gears 56. While a pulley and belt arrangement 60-64 is shown, it is within the purview of the invention to provide a chain and gear arrangement driven from the power source or motor 66. A solenoid type switch arrangement of conventional construction may perform as a lock or stop on the centrally located gear 52 so that the table 12 may be secured in a given orientation between the vertical and horizontal orientations. An inertia device or adjustable resistance device cooperating with the motor 66 and/or the elements 46-66 is included to prevent the table from descending from the vertical to the reclining or horizontal orientation too rapidly, which device may be a simple friction device or brake shoe (as well known and not shown) on the drive shaft 50.

The embodiment of the invention shown in FIG. 4 includes a reclining radiographic table arrangement 70 including a table 72 having a surface 74, a cassette receiving recess 76, the table 72 being supported by a rotatably mounted 24 inch wheel 78 mounted on a shaft 80 supported by brackets or frame 82 at the central portion of the lower end of the table. The frame 82 supports an L member 86 coupled to a standing platform 88 by a hinge member 90. The table 72 is similarly mounted from a rack arrangement 92 by rolling engaging members 94, 96 corresponding in mechanical function with rolling members 14, 16 described above. This arrangement provides that the table 72 has an approximate 24 inch height at full reclined position (not shown) and that the wheel 78 extends from the wall 20 a lesser distance than the embodiment disclosed in FIGS. 1–3.

FIGS. 5 and 6 illustrate a reclining radiographic table arrangement 100 that takes up less space than the embodiments of FIGS. 1-4, inclusive, when the arrangement is in its vertical position. For example, the table surface 102 is about 14 inches or less, displaced from the wall 20 and can be set to give variable table heights depending on the setting of the rack gears 56 on the wall and is provided with floor engaging wheels 106 connected to a folding platform 108 shown in FIGS. 5 and 6. A second set of wheels 110 will engage the floor 112 as the table moves from vertical position toward horizontal position. The wheels 110 are journaled at the outer end of pivotal struts 109 and the wheels 110 are raised and lowered by a fluid pressure operated piston and cylinder assembly 111 or mechanical type lift device. FIG. 6 shows the shaft 116 and the pulley arrangement 118 at their lowermost point along the rack 120, similar in construction to the of rack 18 described above. However, FIG. 6 illustrates the table surface 102, in phantom lines, being at an inclined position for making radiographic observations on the radiographic film or cassettes (not shown).

FIG. 6 also shows a mechanical arrangement 121 for raising the table wheels to support the table in horizontal position comprising a reel 122 mounted to a side of the rack 120 and including a crank arm (not shown) to wind and unwind the reel 122. The reel takes up and lets out the cable 123 as the table 100 is raised and lowered accordingly, the reel being spring loaded for automatic retrieval (not shown) and the reel having a ratchet co-operating with the crank arm to wind, control the amount of the length of the cable 123 and the unwind operations, such that the final height of the table 100 is controllably repositionable at stages between the vertical and the horizontal positions of the table. The cable 123 passes around a pulley 124 with its end coupled to an intermediate position of a bar 125 extending between and interconnecting the pivotal struts 109. This provides precise control in positioning and repositioning the inclined posture of the table 100. Also, the struts 109 are pivotally mounted from the table by a spring loaded axle 113 for urging the pivotal struts 109 toward the table and in bringing the wheels 110 back toward the table as the table returns to its vertical position of orientation. As the table is moved from a vertical or a horizontal orientation to an inclined position, the wall end of the table 100 will stop at a predetermined level of orientation at a given length of the cable 123. At this point the cable length can be adjusted by turning the reel 122 to bring the table to the precise and exact horizontal position desired. Once set and adjusted, it is possible to provide for the table automatically to return to the horizontal position each time the table 100 is inclined or reclined. In view of the motor driven pulley arrangement 118, it is possible to utilize merely the crank arm with reel 122 and then the mechanical arrangement 121 may be located within the side or lateral margins of the rack 120.

The mechanical arrangement 121 may be also positioned lateral of the rack 120 to augment operation of the motor driven pulley arrangement 118.

FIG. 7 illustrates ankle bar 130 positioned upon a patient 132 while the surface 102 of the radiographic table 100 is in the horizontal orientation so that the attachment 130 is secured about the ankles of the patient by placing concave recesses or ankle engaging openings 136 about the patient's ankles and connecting a clamp 138 to the far side of the surface 102 of the table and connecting a clamp fastener 140 at the near side of the table surface 102, the attachment is retained in place.

The table assembly 100 may be oriented in inclined or vertical position so that the patient 132 is inverted and then subject to being X-rayed by X-ray source (not shown) so that the radiographic cassettes in recesses 142 can be used and then it can be determined how much of the scoliotic bend of the spine could be attributable to any gravitational pull upon the patient 132 not present in the inverted position but otherwise imposed upon the patient when he is normally standing free. The table in its displacement from horizontal orientation to vertical orientation or reversed can be stopped at any position intermediate the two limits of movement for facilitating alignment of specific views made upon the radiographic cassettes in the recess 142 so that these specific views are taken. For example, the taking of such an X-ray of the superior body surface of the sacrum, such as the sacral base X-ray, would be easy to accomplish with the table of the present invention. The table is easily reclined to any angle necessary to take this view while maintaining weight bearing upon the feet, but it has been theorized that upon hanging by the arms or the ankles, and being X-rayed, the curve remaining on the X-ray could be attributed to structural changes. Within the scope of the invention, the table could be fully reclined, the patient placed upon it, the ankle bar attachment 130 affixed for holding down the ankles and adjacent portions of the patient 132 against the table and then by raising the table up and at any degree of inversion desirable, X-rays would be obtained for medical, chiropractic, osteopathic or other analysis and evaluation. While it is known that equipment is provided for taking standing X-rays, a horizontal table provided for taking prone or supine X-rays and a Trendelenburg table for taking X-ray or radiographic views at various inclines, by means of the present invention there is provided an arrangement for utilizing full-length or 14×36 buckies and having a mechanism provided for moving the bucky or radiographic recess for heights according to any various sized patients. The table could be stopped in semi-reclining position providing for better table and X-ray tube angles for specific radiographic views, especially of the spine.

According to the present invention, there is provided an assembly having application in medical, chiropractic and osteopathic practice, but is particularly useful for chiropractic examination and evaluation of scoliotic X-rays, 14×36 X-rays, sacral base or other specific cervical X-rays. An important advantage of this invention is to enable a single unit to be installed rather than a conventional straight table supported stationarily on the floor in predetermined relation to a tubestand and tubehead and a conventional wall frame or table normally oriented in alignment with one end of the floor table so that a single tubehead can be used. This invention will not only perform all of the functions of the two conventional units but also additional functions resulting from the capability of the table being adjustable to any inclined position from vertical to horizontal.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A reclining radiographic table including an upright elongated guide structure for support with its lower end adjacent a horizontal support surface, an elongated generally horizontal bed table, support wheel means mounted from one end of said bed table for vertical adjustment relative to said one end between upper and lower positions retracted upwardly toward and projected downwardly from said bed table one end, guide means mounting the other end of said bed table from said guide structure for guided movement therealong, first force means operably connected between said guide structure and said other table end for adjustable positioning of said other table end along said guide structure, said wheel means being provided for rolling support from and movement along said horizontal support surface away from said guide structure upon downward shifting of said other end of said bed table along said guide structure from an upper position with said bed table disposed upright toward a lower position with said bed table generally horizontally disposed, biasing means yieldingly biasing said wheel means toward said upwardly retracted position, and elevation adjustment means operatively connected to said wheel means for adjustably positioning said wheel means, against the biasing action of said biasing means, between said retracted and projected positions, whereby the elevational height of said bed table relative to said support structure, when said bed table is inclined and said bed table is horizontally disposed, may be adjusted.

2. The table of claim 1 wherein said first force means includes rack gear means extending along said guide structure and reversible motor driven pinion gear means journalled from said bed table and meshed with said rack gear means.

3. The table of claim 1 wherein said elevational adjustment means includes fluid motor means operatively connected between said bed table and said wheel means for selectively adjusting said wheel means relative to said one bed table end.

4. The table of claim 1 wherein said elevational adjustment means includes flexible cable means operatively connected between said guide structure and wheel means and operative to automatically downwardly displace said wheel means from said retracted position toward said projected position responsive to movement of said one end of said table away from said guide structure.

5. The table of claim 4 wherein said cable means includes means operative to adjust the effective length thereof, wherein the elevational adjustment of said wheel means relative to said bed table may be adjusted for a given angular positioning of said bed table relative to said horizontal support surface as determined by the adjustable positioning of said other end of said bed table along said guide structure.

* * * * *